(12) United States Patent
Chang

(10) Patent No.: US 9,308,176 B2
(45) Date of Patent: Apr. 12, 2016

(54) LESS ABUSABLE PHARMACEUTICAL PREPARATIONS

(75) Inventor: Rong-Kun Chang, Rockville, MD (US)

(73) Assignee: Supernus Pharmaceuticals, Inc, Rockville, MD (US)

( * ) Notice: Subject to any disclaimer, the term of this patent is extended or adjusted under 35 U.S.C. 154(b) by 1831 days.

(21) Appl. No.: 11/250,309

(22) Filed: Oct. 14, 2005

(65) Prior Publication Data

US 2006/0083690 A1  Apr. 20, 2006

Related U.S. Application Data

(60) Provisional application No. 60/619,589, filed on Oct. 15, 2004.

(51) Int. Cl.
| | |
|---|---|
| *A61K 9/16* | (2006.01) |
| *A61K 9/50* | (2006.01) |
| *A61K 9/20* | (2006.01) |
| *A61K 9/28* | (2006.01) |
| *A61K 47/48* | (2006.01) |

(52) U.S. Cl.
CPC ............. *A61K 9/5015* (2013.01); *A61K 9/1617* (2013.01); *A61K 9/1652* (2013.01); *A61K 9/2013* (2013.01); *A61K 9/2054* (2013.01); *A61K 9/2072* (2013.01); *A61K 9/2866* (2013.01); *A61K 9/5042* (2013.01); *A61K 47/48184* (2013.01)

(58) Field of Classification Search
CPC ....... A61K 9/16; A61K 9/1664; A61K 9/167; A61K 9/1676; A61K 9/1652; A61K 9/1629; A61K 9/1635
USPC ........................... 424/489, 434, 490, 464, 465
See application file for complete search history.

(56) References Cited

U.S. PATENT DOCUMENTS

| | | | | |
|---|---|---|---|---|
| 3,079,303 | A * | 2/1963 | Raff et al. ...................... | 424/500 |
| 3,383,283 | A | 5/1968 | Brindamour | |
| 4,070,494 | A | 1/1978 | Hoffmeister et al. | |
| 4,401,672 | A | 8/1983 | Portoghese | |
| 4,457,933 | A | 7/1984 | Gordon et al. | |
| 4,834,965 | A * | 5/1989 | Martani et al. ................ | 424/488 |
| 5,162,341 | A | 11/1992 | Cook | |
| 5,236,714 | A | 8/1993 | Lee et al. | |
| 5,958,458 | A * | 9/1999 | Norling et al. ................ | 424/490 |
| 6,124,282 | A | 9/2000 | Sellers et al. | |
| 6,159,501 | A * | 12/2000 | Skinhoj .......................... | 424/461 |
| 6,187,341 | B1 | 2/2001 | Johnson et al. | |
| 6,228,863 | B1 | 5/2001 | Palermo et al. | |
| 6,277,384 | B1 | 8/2001 | Kaiko et al. | |
| 7,141,250 | B2 | 11/2006 | Oshlack et al. | |
| 7,214,385 | B2 | 5/2007 | Gruber | |
| 2003/0064099 | A1 * | 4/2003 | Oshlack et al. ............... | 424/465 |
| 2003/0064122 | A1 | 4/2003 | Goldberg et al. | |
| 2003/0091635 | A1 | 5/2003 | Baichwal et al. | |
| 2004/0228802 | A1 | 11/2004 | Chang et al. | |
| 2006/0018837 | A1 * | 1/2006 | Preston et al. ............... | 424/10.4 |
| 2006/0083690 | A1 | 4/2006 | Chang | |

FOREIGN PATENT DOCUMENTS

| | | | | |
|---|---|---|---|---|
| EP | 0 225 615 | A2 * | 6/1987 | ............... A61K 9/22 |
| EP | 1382331 | A1 * | 1/2004 | |

OTHER PUBLICATIONS

S. El-Kheshern et al, Coating charcoal with polyacrylate-polymethacrylate copolymer for haemoperfusion III: The effect of the coat thickness on the adsorption capacity of the coated charcoal and its adsorption to small and middle size molecules, J Microencapsulation, 1995, vol. 12, No. 5, 505-514.*

Matschiner et al. "Characterization of ion pair formation between erythromycin and lipophilic counter ions," Pharmazie, 1995, vol. 50, pp. 462-464.

Rao et al., "Effect of Sodium Lauryl Sulfate on the Release of Rifampicin from guar gum Matrix," Indian Journal of Pharmaceutical Sciences, Sep.-Oct. 2000, pp. 404-406.

Wells et al., "Effect of Anionic Surfactants on the Release of Chlorpheniramine Maleate from an Inert, Heterogeneous Matrix," Drug Development and Industrial Pharmacy, 1992, vol. 18, No. 2, pp. 175-186.

Non-Final Office Action mailed on May 3, 2006 in U.S. Appl. No. 10/435,597, 8 pages.

Final Office Action mailed on Oct. 1, 2007 in U.S. Appl. No. 10/435,597, 10 pages.

Advisory Action mailed on Mar. 13, 2008 in U.S. Appl. No. 10/435,597, 3 pages.

Non-Final Office Action mailed on Jun. 11, 2008 in U.S. Appl. No. 10/435,597, 9 pages.

Non-Final Office Action mailed on Jan. 9, 2009 in U.S. Appl. No. 10/435,597, 10 pages.

Non-Final Office Action mailed on Feb. 23, 2010 in U.S. Appl. No. 10/435,597, 9 pages.

Final Office Action in U.S. Appl. No. 10/435,597 dated Oct. 1, 2007.
Office Action in U.S. Appl. No. 10/435,597 dated May 3, 2006.

* cited by examiner

*Primary Examiner* — Michael G Hartley
*Assistant Examiner* — Micah-Paul Young
(74) *Attorney, Agent, or Firm* — Foley & Lardner LLP; Sunit Talapatra

(57) ABSTRACT

The present invention is directed to pharmaceutical compositions of psychoactive drugs having a reduced potential for abuse and methods of reducing the potential for abuse of dosage forms of prescription psychoactive drugs.

2 Claims, No Drawings

LESS ABUSABLE PHARMACEUTICAL PREPARATIONS

FIELD OF THE INVENTION

This invention relates to dosage forms of prescription psychoactive drug formulations having a reduced potential for abuse and to methods of reducing the potential for abuse of dosage forms of prescription psychoactive drugs.

BACKGROUND OF THE INVENTION

Prescription psychoactive drugs can help patients manage chronic or severe pain, restore emotional or behavioral balance, control sleep disorders, or fight obesity. When such prescription medications are abused, however, the consequences, including addiction, can be dangerous, even deadly. The risks associated with abuse of three classes of commonly abused prescription drugs, i.e., opioids; central nervous system (CNS) depressants, including sedatives and tranquilizers; and stimulants, are well documented.

Opioids include morphine, codeine, and related drugs such as oxycodone (Percodan and OxyContin), hydrocodone (Vicodin), and meperidine (Demerol) and are commonly prescribed to relieve pain. Taken as prescribed, opioids can be used to manage pain effectively without untoward side effects. Chronic use of opioids can result in tolerance, which means that users must take higher doses to achieve the same effects. Long-term use also can lead to physical dependence and addiction. Withdrawal can occur when an individual discontinues use of the drugs. Withdrawal symptoms can include restlessness, muscle and bone pain, insomnia, diarrhea, vomiting, cold flashes with goose bumps, and involuntary leg movements. Individuals who are addicted to opioids are more likely to overdose on the drugs, which could be fatal.

Among the most commonly prescribed CNS depressants are barbiturates, such as mephobarbital (Mebaral) and pentobarbital sodium (Nembutal), which are prescribed to treat anxiety, tension, and sleep disorders; and benzodiazepines, such as diazepam (Valium) and alprazolam (Xanax), which typically are prescribed to treat anxiety, acute stress reactions, and panic attacks. Other benzodiazepines, such as triazolam (Halcion) and estazolam (ProSom), are prescribed for short-term treatment of sleep disorders. Although the various classes of CNS depressants work differently, they all produce a beneficial drowsy or calming effect in individuals suffering from sleep disorders or anxiety. However, if one uses these drugs over a long period of time, the body will develop tolerance, and larger doses will be needed to achieve the initial effects. In addition, continued use can lead to physical dependence and, when use is reduced or stopped, withdrawal. Both barbiturates and benzodiazepines have the potential for abuse and should be used only as prescribed. As with opioids, an overdose of these drugs can be fatal.

Stimulants increase heart rate, blood pressure and metabolism, provide feelings of exhilaration and energy, and increase mental alertness. Stimulants such as methylphenidate (Ritalin) and dextroamphetamine (Adderall and Dexedrine) are prescribed for the treatment of narcolepsy, attention-deficit/hyperactivity disorder, and depression that has not responded to other treatments. They also may be used for short-term treatment of obesity. Individuals may become addicted to the sense of well-being and enhanced energy that stimulants can generate. Taking high doses of stimulants repeatedly over a short time, however, can lead to feelings of hostility or paranoia. Additionally, taking high doses of stimulants may result in dangerously high body temperatures and an irregular heartbeat.

Abuse potential of these three classes of drugs is of major concern. This is specially true for opioids and stimulants and hence they are classified by the Drug Enforcement Agency (DEA) as Schedule II drugs (substances that have a high potential for abuse with severe liability to cause psychic or physical dependence, but have some approved medical use).

Various dosage forms of psychoactive drugs for medical use are available or possible. These include capsules, tablets, transdermal patches and liquid suspensions. For example, methylphenidate (Ritalin) is available in oral, tablet and extended-release tablet dosage forms. Dextroamphetamine (Adderall) is available in immediate-release tablet and extended-release capsule dosage forms. Methylphenidate, amphetamine, fentanyl, 3-methyl fentanyl, morphine, etorphine, etc. can be incorporated into transdermal patches. A fentanyl patch (Duragesic) is already in the marketplace and a methylphenidate patch (Methypatch) is under FDA review. Liquid suspensions of drugs in immediate release and sustained release forms are also possible. A sustained release system can be formulated by using drug ion-exchange complex particles with a further coating of ethyl cellulose. The ion-exchange technology makes reliable liquid controlled-release possible for many ionic drugs, which include amphetamine, methylphenidate, hydrocodone, codeine, morphine, and the like.

These various dosage forms provide valuable medical benefits when properly taken or administered, but also have a high potential for abuse. For example, sustained release dosage forms are abused by crushing or chewing and then swallowing or snorting or by mixing or dissolving in water or the like and then injecting. Transdermal patches can be chewed to provide a quick onset via buccal, sublingual, or oral absorption of the controlled substances. In addition, a significant drug residue after normal administration of the patches is quite common. Such residue can be extracted and concentrated for abuse. Liquid suspensions can be similarly concentrated and abused.

In view of these problems, new and improved dosage forms of psychoactive drugs having decreased abuse potential are desired. Several approaches to reducing the abuse potential of dosage forms of drugs can be found in U.S. patents. These include, for example, the incorporation of an opioid antagonist into a dosage form (U.S. Pat. Nos. 4,401,672, 4,457,933, 5,162,341, 5,236,714, 6,277,384 and 6,228,863), the use of cytochrome P450 2D6 enzyme inhibitor (U.S. Pat. No. 6,124, 282), and the incorporation of a water soluble/gelable material into a dosage form (U.S. Pat. No. 4,070,494). However, these approaches still are far from ideal in terms of the effectiveness of deterring someone from abusing the medication by snorting or smoking or improper oral administration.

OBJECT OF THE INVENTION

It is an object of the present invention to reduce the potential for abuse of dosage forms of psychoactive drugs and other drugs of abuse and to provide dosage forms of psychoactive drugs having a reduced potential for abuse. More particularly, it is an object of the present invention to provide oral dosage forms of opioids, CNS depressants and stimulants that have increased effectiveness in deterring abuse by snorting/injecting or the like.

DETAILED DESCRIPTION OF THE INVENTION

The psychoactive drug (i.e., a drug that affects the central nervous system) of the dosage form of the present invention is not particularly limited insofar as the drug is approved for medical use in dosage form and has a potential for abuse. The drug includes opioids, central nerve system (CNS) depressants and stimulants such as, for example, drugs sold commercially under the trademarks Adderall XR, Matadate CD, Kadian, Oramorph SR, MS Contin, Oxycontin and the like, each alone or in combination.

Most narcotic drugs and stimulants, e.g., amphetamine sulfate, amphetamine aspartate, amphetamine saccharate, morphine sulfate, oxycodone hydrochloride, methylphenidate hydrochloride, etc., are basic drugs containing positively charged amine group. One objective of this invention exploits this chemical property. These basic drugs can react with a negatively charged agent (also referred to herein as "deterrent substances") to form an ion-associated complex in an aqueous environment. The absorption of these ion-associate complexes is hindered due to their resulting lowered water solubility.

In one aspect, anionic surface-active agents, such as sodium lauryl sulfate and sodium dioctyl sulfosuccinate are used to interact with positively charged amine drugs to form poorly water-soluble complexes. This is derived from, for example Wells et al., who investigated the effect of anionic surfactants on the release of chlorpheniramine maleate from an inert, heterogeneous matrix, and found that the formation of a poorly water-soluble complex between chlorpheniramine maleate and the anionic surfactant slowed the release to a minimum at low concentrations of surfactant. (Drug Dev. Ind. Pharm., 1992, 18(2), 175-186). Further, Rao et al. published an article on "Effect of sodium lauryl sulfate on the release of rifampicin from guar gum matrix" in Indian Journal of Pharmaceutical Sciences, 2000, September-October, 62(5), 404-406. They also observed that as the concentration of sodium lauryl sulfate increased to 15%, the release progressively slowed to a minimum, which is attributed to the formation of a poorly soluble complex. Still further, Matschiner et al. characterized ion pair formation between erythromycin and sodium lauryl sulfate and confirmed the assumption of a complex formation in the molar ratio 1:1. (Pharmazie, 1995, 50(July), 462-464).

In addition, anionic surfactants, such as sodium lauryl sulfate, are known to interact with hydrophilic matrix polymers, such as hydroxypropyl methylcellulose, to form a more viscous gel in water. This more viscous gel layer generally results in a slower dissolution rate.

In a further aspect, there are many ionic polymers, such as acrylic acid polymers, sodium alginate, sodium carboxyl methylcellulose, styrene divinyl benzene sulfonates and carrageenan, that can also complex with positively charged drugs. The complex is held together by ionic attraction between the amine group of drug compound and the carbonyl group of the polymers. When dispersed into water, the hydrophilic nature of these polymers also imparts the viscosity to the medium, which further hinders the release and absorption of the drug.

In another aspect of the present invention, positively charged amine drugs can react with a negatively charged dye such as allura red, amaranth, brilliant blue, canthaxanthin, carmine erythrosine, indigo carmine, ponceau 4R, quinoline yellow, tartrazine, thymol blue, bromothymol blue, bromocresol green, bromopyrogallol red, phenol red, cresol red to form an ion-association complex in an aqueous solution, which prevents preferential extraction of the drug.

Moreover, alkaline agents, such as sodium bicarbonate, calcium carbonate, meglumine, and calcium phosphate, can be used to convert salt forms of amine drugs to free base. Generally, free bases have much lower solubility than their salts. For example, the aqueous solubilities of morphine sulfate at pH 1.5 and 7.4 are 90.1 mg/mL and 1.3 mg/mL, respectively. The aqueous solubilities of oxycodone hydrochloride at pH 1.5 and 7.4 are 182.1 mg/mL and 6.1 mg/mL, respectively. The drastic decrease in aqueous solubility due to the addition of alkaline agents may be used to avoid the fast dissolution of the drug and to minimize the rush effect, for which drug abusers commonly have a craving.

In yet a further aspect of the invention, the deterrent substance can be an absorbent material, such as activated charcoal, magnesium aluminum silicate, or activated alumina, for example. These substances have been used in the past to physically absorb drugs, especially in the detoxification and solid extraction fields. Thus, these may also be useful in the present invention to minimize abuse potential.

The goal in using any of the above materials in a dosage form is to make the abusive drug less available to the human system, so that little or no "high" is obtained. These dosage forms, therefore, are not desirable to a drug abuser.

Snorting and smoking for substance abuse are widespread and the use of substances that ionically interact with an abuse-potential drug product can be an effective means to deter the drug abuse. The substances, such as those mentioned above are to be incorporated into the dosage forms of the abuse-potential drugs in such a manner that the deterrent substance does not exhibit its deterrent effect when a dosage form of the drug is properly administered, but exhibits a deterrent effect when the dosage form is chewed, crushed or chemically extracted for nasal (snorting), inhalation (smoking), oral, buccal or sublingual administration or injected.

The deterrent substance can be incorporated into granules, beads, or mini-tablets, or the like, as a separate entity from the drug(s) in the dosage form, which are subsequently coated with a suitable barrier coating to prevent against leakage of the deterrent substance and to minimize or prevent absorption of the deterrent substance under normal dosage administration conditions. These granules/beads/mini-tablets are combined with the drug of interest into the dosage form (e.g., capsule, tablet, etc.).

The sizes of the granules, beads and mini-tablets is not limited as long as the granules can be incorporated into the dosage forms of the invention. Typically, the granules and beads have a size of 50 µm to 4000 µm. The mini-tablets have a size that is typically significantly smaller than common tablets (>5/32 inch diameter).

When granules, beads or mini-tablets containing the deterrent substance(s) and not containing a drug are encapsulated or otherwise combined with granules, beads or mini-tablets containing an active pharmaceutical ingredient (API), the granules, beads or mini-tablets are preferably of the same size to make it difficult for the respective beads to be distinguished and separated.

When used in a transdermal patch formulation, the deterrent substance(s) can be used in the form of the above-described granules, beads, or mini-tablets coated with a suitable barrier coating.

The at least one deterrent substance is/are used in a total amount of from 10 to 70% by weight and, preferably, 10 to 50% by weight and, most preferably, 10 to 40% by weight based on the weight of a dosage form of the pharmaceutical formulation into which the agent is incorporated. The agent can be one or more of the above-noted substances. Having the deterrent substance(s) in non-releasable form is preferred, because it will not be released from an intact unit (e.g., heavily coated mini-tablets or pellets containing the substance(s)), has no pharmacological effect, and has no impact on the release profile of the active ingredient.

The granules, beads, mini-tablets and tablets of the deterrent substance(s) can be made by various known pharmaceutical processes, such as roller compacting, and solution/slurry/powder layering in a fluid bed or other appropriate coating equipment, and compressing in a tablet press. In a particularly preferred embodiment, core seeds such as non-pareil seeds are coated with a layer of the deterrent substance(s) and a barrier coating is applied to the layered core seeds. Alternatively, the core of a granulate, bead or mini-tablet is composed primarily of the deterrent substance(s), and the core is coated with such a barrier coating.

The barrier coating applied to the granules, beads or mini-tablets containing the deterrent substance(s) to minimize or prevent leakage of the substance(s) and to minimize absorption of the substance(s) under normal conditions of dosage administration can be a protective coating, enteric coating or sustained release coating or various combinations of these coatings.

In a preferred embodiment, granules, beads or mini-tablets containing the deterrent substance(s) and not containing the drug are coated with a non-dissolving, pharmaceutically acceptable polymer coating that does not dissolve or release under conditions existing in the GI tract. With such a coating, the deterrent substance(s) is/are not released in the human body when properly administered and is/are released only when a drug formulation including the granules, beads or mini-tablets coated with the non-dissolving coating is crushed for non-prescribed purposes. In this way, also, the deterrent substance(s) will not interfere (i.e. form complexes with the drug) with the action of the drug under normal administration routes.

The barrier coating may be applied by conventional coating techniques such as pan coating or fluid bed coating using solutions of polymers in water or suitable organic solvents or by using aqueous polymer dispersions.

Materials useful as a protective coating are well-known in the art and include, for example, cellulose derivatives such as hydroxyethyl cellulose, hydroxypropyl cellulose, hydroxypropyl methylcellulose, polyvinylpyrrolidone, poly(butyl methacrylate (2-dimethyl aminoethyl) methacrylate, methyl methacrylate), and polyvinylpyrrolidone/vinyl acetate copolymer. The suggested coating levels are from 1 to 6%, preferably 2-4% (w/w).

The enteric coating layer can be any pH-sensitive polymer, which dissolves at a pH greater than 4.5, after a certain delayed time, or after the coated unit passes through the stomach. The preferred delay time is in the range of two to six hours. Suitable enteric polymers include cellulose acetate phthalate, cellulose acetate trimellitate, hydroxypropyl methylcellulose phthalate, polyvinyl acetate phthalate, carboxymethylethylcellulose, and co-polymerized methacrylic acid/methacrylic acid methyl esters such as, for instance, materials sold under the trademarks EUDRAGIT L100, EUDRAGIT L100-55, EUDRAGIT L 30 D-55 or EUDRAGIT S100 or similar compounds used to obtain enteric coatings. The suggested coating levels are from 5 to 30%, preferably 10-20% (w/w).

The pharmaceutically acceptable coating that does not dissolve in the GI tract includes cellulose acetate, cellulose acetate butyrate, cellulose acetate propionate, ethyl cellulose, poly(ethyl acrylate), poly (methyl methacrylate), and poly (trimethylammonioethylmethacrylate chloride). Suitable coating levels are those that prevent premature leakage of the deterrent substance(s) and depend on the coating used. Coating levels range, for example, from 1 to 60% (w/w).

In one embodiment, the core containing the deterrent substance is coated with an acid soluble coating, such as Eudragit E100, to which is applied another coating of an alkaline soluble coating, such as Eudragit FS 30. As such, the material in the core will not be released in the GI tract, because when the particle reaches the relatively alkaline lower GI tract where the outside layer will dissolve, the inside coating, which is soluble in acid, will not dissolve.

An overcoating layer can further optionally be applied to the composition of the present invention. OPADRY®, OPADRY II® (sold by Colorcon) and corresponding color and colorless grades from Colorcon can be used to protect the pellets from being tacky and to provide color to the product. Additionally, Kollicoat IR (sold by BASF) with or without colorants and opacifiers can be used as an overcoating layer. The suggested levels of protective or color coating are from 1 to 6%, preferably 2-3% (w/w).

The following examples illustrate some aspects of the present invention, it being understood that the present invention is not limited in scope or spirit to the examples.

EXAMPLES

Example 1

Preparation of Beads Containing Sodium Lauryl Sulfate

Sodium lauryl sulfate (200 grams) is granulated with talc (50 grams) and microcrystalline cellulose (750 grams) using isopropyl alcohol as a granulating fluid in a high shear granulator. The wet mass is extruded using 1.2 mm screen size and extruder speed setting around 30 rpm to 50 rpm. The extruded material is spheronized in a spheronizer/marumarizer at speed setting around 400 rpm to 1000 rpm. The spherical pellets generated are dried in an oven at 40 degree C.

Example 2

Preparation of Cellulose Acetate Coated Pellets Containing Sodium Lauryl Sulfate Cellulose acetate (60 grams) is dissolved in a mixture of acetone and ethyl acetate (1:1 ratio and total 1200 grams) using a stirring paddle. Cellulose acetate coating solution is sprayed onto sodium lauryl sulfate beads (540 grams) in a fluid bed using a Wurster column. The spray rate is around 5 gram/min to 15 gram/min. The Inlet temperature is set at 40 degree C. to 50 degree C. and the bed temperature is maintained at 30 degree C. to 35 degree C. Air volume is around 5 to 8 meters per second to maintain a proper fluidization.

Example 3

Preparation of Mini-tablets Containing Sodium Dioctyl Sulfosuccinate and Dowex 50X8-200

Sodium dioctyl sulfosuccinate (150 grams), Dowex 50X8-200 (350 grams), microcrystalline cellulose (480 grams) are blended in a V-shaped blender for 10 minutes. Magnesium stearate (10 grams) and silicon dioxide (10 grams) are added to the powder blend and blended for 5 minutes. The lubricated powder blend is compressed into mini-tablets using a rotary press with 7/32" round tooling. Target tablet weight is 90 mg; the target tablet hardness is 5 kp; the friability is less than 0.8%.

Example 4

Preparation of Cellulose Acetate Coated Mini-tablets Containing Sodium Dioctyl Sulfosuccinate and Dowex 50X8-200

Cellulose acetate (60 grams) is dissolved in a mixture of acetone and ethyl acetate (1:1 ratio and total 1200 grams) using a stirring paddle. Cellulose acetate coating solution is sprayed onto sodium dioctyl sulfosuccinate/Dowex 50X8-200 mini-tablets (540 grams) in a side-vented pan. The pan speed is around 10 rpm to 20 rpm. The spray rate is around 5 gram/min to 15 gram/min. The Inlet temperature is set at 40 degree C. to 50 degree C. and the bed temperature is maintained at 30 degree C. to 35 degree C. Air volume is around 30 cfm to 45 cfm.

The beads and mini-tablets from the Examples 2 and 4 can be overcoated to have exactly the same appearance as the active beads or mini-tablets. Subsequently, the beads and mini-tablets can be encapsulated with the active units.

What is claimed is:

1. A dosage form having reduced abuse potential comprising:
    (a) a first population of granules, beads or minitablets comprising a psychoactive drug, and
    (b) a second population of drug-free granules, beads or minitablets comprising:
        (i) a core comprising at least one deterrent substance selected from the group consisting of activated charcoal and alumina and
        (ii) a coating surrounding the core, wherein said coating does not dissolve in the gastrointestinal tract and comprises a polymer selected from the group consisting of cellulose acetate, cellulose acetate butyrate, cellulose acetate propionate, ethyl cellulose, poly(ethyl acrylate), poly(methyl methacrylate), and poly(trimethylammonioethylmethacrylate chloride),
    which is further coated with an alkaline soluble coating comprising a polymer selected from the group consisting of cellulose acetate phthalate, cellulose acetate trimellitate, hydroxypropyl methyl cellulose phthalate, polyvinyl acetate phthalate, carboxymethylethylcellulose, and co-polymerized methacrylic acid/methacrylic acid methyl esters, and
    wherein the deterrent substance does not interact with the drug when properly administered.

2. A dosage form having reduced abuse potential comprising:
    (a) a first population of granules, beads or minitablets comprising a psychoactive drug, and
    (b) a second population of drug-free granules, beads or minitablets comprising:
        (i) a core comprising at least one ionically binding substance selected from the group consisting of styrene-divinyl benzene sulfonates and
        (ii) a coating surrounding the core, wherein said coating is a non-dissolving coating comprising a polymer selected from the group consisting of cellulose acetate, cellulose acetate butyrate, cellulose acetate propionate, ethyl cellulose, poly(ethyl acrylate), poly(methyl methacrylate), and poly(trimethylammonioethylmethacrylate chloride),
    which is further coated with an alkaline soluble coating comprising a polymer selected from the group consisting of cellulose acetate phthalate, cellulose acetate trimellitate, hydroxypropyl methyl cellulose phthalate, polyvinyl acetate phthalate, carboxymeth lethylcellulose, and co-polymerized methacrylic acid/methacrylic acid methyl esters,
    wherein the ionically binding substance forms an ion-associated complex with the drug in an aqueous environment so to lower the solubility of the drug compared to its unbound form, but does not interact with the drug when properly administered.

* * * * *